(12) United States Patent
Giffels et al.

(10) Patent No.: US 6,458,954 B2
(45) Date of Patent: Oct. 1, 2002

(54) PROCESS FOR PREPARING PIPERIDINES

(75) Inventors: Guido Giffels, Bonn (DE); Herbert Diehl, Leverkusen (DE); Georg Martin, Langenfeld (DE); Lutz Frohn, Erkrath (DE); Erich Hammerschmidt, Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/846,003

(22) Filed: Apr. 30, 2001

(30) Foreign Application Priority Data

May 8, 2000 (DE) .......................... 100 22 369

(51) Int. Cl.⁷ ................... C07D 211/02; C07D 211/60
(52) U.S. Cl. .................. 546/113; 546/185; 546/245
(58) Field of Search ................. 546/185, 245, 546/113

(56) References Cited

U.S. PATENT DOCUMENTS

| | | | |
|---|---|---|---|
| 4,990,517 A | 2/1991 | Petersen et al. | 514/300 |
| 5,059,597 A | 10/1991 | Petersen et al. | 514/224.5 |
| 5,374,728 A | * 12/1994 | Kampmann et al. | 546/185 |
| 5,416,096 A | 5/1995 | Petersen et al. | 514/312 |
| 5,607,942 A | 3/1997 | Petersen et al. | 546/200 |
| 5,654,318 A | 8/1997 | Takemura et al. | 514/314 |
| 5,942,104 A | 8/1999 | Miller | 208/28 |

OTHER PUBLICATIONS

Hiroaki et al, JP2001081477 (abstract), Mar. 27, 2001.*

Heterogenous Catalysis for the Synthetic Chemist, New, York, (month Unavailable) 1996, Chapter, 17 pp. 421–424, Hydrogenation IV: Aromatic Compounds.

* cited by examiner

*Primary Examiner*—Alan L. Rotman
*Assistant Examiner*—Raymond Covington
(74) *Attorney, Agent, or Firm*—Joseph C. Gil; Richard E. L. Henderson

(57) ABSTRACT

Piperidines are prepared in an advantageous manner by catalytic hydrogenation of activated pyridines in the presence of palladium catalysts if the palladium catalyst is palladium-on-carbon and the solvents are aromatic hydrocarbons.

8 Claims, No Drawings

PROCESS FOR PREPARING PIPERIDINES

BACKGROUND OF THE INVENTION

The present invention relates to an improved process for preparing piperidines by hydrogenation of the ring of the corresponding pyridines.

Piperidines are intermediates for the preparation of pharmaceutically active compounds (see, for example, EP-A 603,887 and EP-A 350,733, particularly pages 2 and 17). Accordingly, they have to be available in a form which is as pure as possible.

Activated piperidines are usually hydrogenated to the corresponding piperidines using palladium catalysts in alcoholic solvents, such as methanol, ethanol, isopropanol, or ethylene glycol monomethyl ether (see *Heterogenous Catalysis for the Synthetics Chemist*, New York 1996, Chapter 17, pages 421 to 424 and EP-A 350,733, particularly pages 65 and 66). The reaction mixture is generally worked up by removing catalyst and solvent. This gives rise to piperidines that must be purified further, for example, by crystallization, distillation, or chromatography. In this manner, undesirable by-products contained in the piperidines are removed. In addition to the expense associated with such a purification, the loss of product that occurs during further purification is disadvantageous, especially since the solvent is difficult to recycle, due to the impurities contained therein.

Accordingly, there is still a need for a process for preparing piperidines that does not require further purification of the product isolated from the reaction mixture.

SUMMARY OF THE INVENTION

This invention, accordingly, provides a process for preparing piperidines comprising catalytically hydrogenating activated pyridines in the presence of a palladium catalyst and aromatic hydrocarbon solvents, wherein the palladium catalyst is palladium-on-carbon.

DETAILED DESCRIPTION OF THE INVENTION

Suitable activated pyridines for use in the process according to the invention are, for example, those of formula (I)

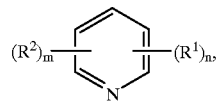

(I)

in which
$R^1$ represents $COOR^3$, $CONH_2$, $CO-NH-COR^3$, or $COOH$ groups or two adjacent $R^1$ groups together represent a $CO-NR^4-CO$ group,
$R^2$ represents linear or branched $C_1-C_{20}$-alkyl,
$R^3$ represents linear or branched $C_1-C_6$-alkyl, phenyl, or benzyl,
$R^4$ represents hydrogen, linear or branched $C_1-C_6$-alkyl, phenyl, or benzyl,
n represents 1 or 2, and
m represents zero, 1, or 2.

If n represents 2, two identical or two different radicals $R^1$ may be present. Likewise, if m represents 2, two identical or different radicals $R^2$ may be present.

Preferably, $R^1$ represents $COO-C_1-C_4$-alkyl or two adjacent $R^1$ groups together represent a $CO-N(benzyl)-CO$ group, $R^2$ represents $C_1-C_4$-alkyl, n represents 1 or 2, and m represents zero or 1.

If activated pyridines of the formula (I) are employed in the process according to the invention, the corresponding piperidines of formula (II)

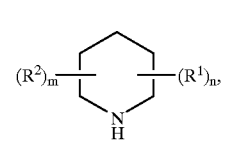

(II)

in which $R^1$, $R^2$, m, and n are as defined under formula (I), are obtained.

The palladium-on-carbon catalysts to be used according to the invention can, for example, be catalysts that comprise from 1 to 10% by weight of palladium on any carbon. Preferably, the catalysts comprise from 2 to 8% by weight of palladium. Suitable catalysts are commercially available.

It is possible to use, for example, an amount of catalyst such that from 0.5 to 30 mmol of palladium are present per mole of activated pyridine. This amount is preferably from 2 to 15 mmol.

Suitable aromatic hydrocarbons are, for example, benzene, toluene, xylenes, and other alkyl aromatics. Preference is given to toluene. Based on 1 mole of activated pyridine, it is possible to use, for example, from 50 to 5000 g of aromatic hydrocarbon (also in the form of mixtures).

The catalytic hydrogenation according to the invention can be carried out, for example, at temperatures in the range from 20 to 200° C. Preference is given to temperatures in the range from 50 to 150° C., particularly those in the range from 60 to 100° C. Suitable pressures are, for example, those in the range from 1 to 200 bar. Preference is given to pressures in the range from 3 to 150 bar, particularly those in the range from 5 to 60 bar.

The simultaneous use of temperatures and pressures close to the upper limit should advantageously be avoided, since there is otherwise a risk of the solvent being co-reduced.

After the catalytic hydrogenation has been carried out, the reaction mixture that is present can be worked up, for example, by removing the catalyst (for example, by filtration) and then removing the aromatic hydrocarbon (for example, by distillation, if appropriate under reduced pressure). Both the catalyst that has been removed and the aromatic hydrocarbon that has been removed can be recycled. If appropriate, fresh catalyst and fresh aromatic hydrocarbon can be added to the recycled catalyst and the recycled aromatic hydrocarbon, respectively.

Following removal of the catalyst and the aromatic hydrocarbon, the piperidines that are prepared are generally present in purities of more than 98%. Accordingly, further purification is not necessary. As is shown in the Comparative Examples, the customary procedure, which employs alcoholic solvents, gives without further purification only piperidines of a purity of about 94%. For the further use of piperidines as intermediates for pharmaceutics, the purity that can be obtained according to the invention is of decisive importance.

It is extremely surprising that, according to the present invention, such an advantageous process has been found, since it was not to be expected from the prior-art literature that high yields and selectivities can be obtained in the heterogeneous catalysis with palladium-on-carbon catalysts in nonpolar solvents. Furthermore, it was to be expected that not only the pyridines employed but also the aromatic hydrocarbons used as solvents should be hydrogenated, resulting not only in contaminated products but also, additionally, in a loss of solvent. However, the latter is negligible.

EXAMPLES

In a 0.7 liter stirred autoclave fitted with stirrer, temperature sensor and riser tube, 163.7 g of pyridine-2,3-dicarboxylic acid N-benzylimide and 6.6 g of 5% by weight palladium-on-carbon were suspended in 256.7 g of toluene. The autoclave was flushed twice with nitrogen and then twice with hydrogen. Under a hydrogen pressure of 5 bar, the autoclave was then heated to 80° C., and the hydrogen pressure was increased gradually to 50 bar, so that the reaction temperature of 80° C. could be maintained. After 50 bar had been reached, stirring was continued at 80° C. for 10 hours. The autoclave was then cooled, the catalyst was removed from the reaction mixture by filtration, and toluene was removed under reduced pressure using a rotary evaporator. This gave 170 g of piperidine-2,3-dicarboxylic acid N-benzylimide in a purity of 98.8% (GC area percent).

Example 2

Example 1 was repeated using 181.7 g of pyridine-2,3-dicarboxylic acid N-benzylimide and hydrogenating at a pressure of 10 bar. This gave 183.2 g of piperidine-2,3-dicarboxylic acid N-benzylimide in a purity of 98.2% (GC area percent).

Example 3

In a 1.3 liter stirred autoclave fitted with stirrer, temperature sensor, and riser tube, 666 g of pyridine-2,3-dicarboxylic acid N-benzylimide and 28.2 g of 5% by weight palladium-on-carbon were suspended in 959 g of toluene. The autoclave was then flushed, hydrogen was introduced, and the autoclave was heated at a reaction temperature of 80° C. as described in Example 1. Work-up of the reaction mixture as described in Example 1 gave 618 g of piperidine-2,3-dicarboxylic acid N-benzylimide in a purity of 98.7% (GC area percent).

Example 4

In a 0.3 liter stirred autoclave fitted with stirrer and temperature sensor, 19.52 g of dimethyl pyridine-2,3-dicarboxylate and 2.25 g of 5% by weight palladium-on-carbon were initially charged in 131 g of toluene. The autoclave was flushed twice with nitrogen and then twice with hydrogen. The autoclave was then heated to 80° C. and, after this temperature had been reached, a hydrogen pressure of 10 bar was applied and the mixture was hydrogenated under these conditions for 4 hours. After the reaction mixture had cooled, the catalyst was separated off by filtration and toluene was removed under reduced pressure using a rotary evaporator. This gave 19.13 g of dimethyl cis-piperidine-2,3-dicarboxylate in a purity of 98.7% (GC area percent).

Comparative Example 1

(Solvent: isopropanol)

Example 2 was repeated except for using 261.7 g of isopropanol instead of toluene. This gave 185.7 g of piperidine-2,3-dicarboxylic acid N-benzylimide in a purity of 94% (GC area percent).

Comparative Example 2

(Solvent: ethylene glycol monomethyl ether)

Example 1 was repeated except for using, instead of toluene, the same amount of ethylene glycol monomethyl ether. This gave 171.1 g of piperidine-2,3-dicarboxylic acid N-benzylimide in a purity of 94.8% (GC area percent).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing piperidines comprising catalytically hydrogenating activated pyridines in the presence of a palladium catalyst and an aromatic hydrocarbon solvent, wherein the palladium catalyst is palladium-on-carbon.

2. A process according to claim 1 wherein the activated pyridines have the formula (I)

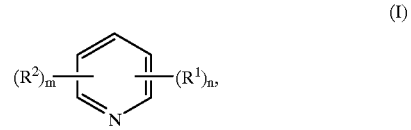

(I)

wherein $R^1$ represents $COOR^3$, $CONH_2$, CO—NH—$COR^3$, or COOH groups or two adjacent $R^1$ groups together represent a CO—$NR^4$—CO group, $R^2$ represents linear or branched $C_1$–$C_{20}$-alkyl or halogen, $R^3$ represents linear or branched $C_1$–$C_6$-alkyl, phenyl, or benzyl, $R^4$ represents hydrogen, linear or branched $C_1$–$C_6$-alkyl, phenyl, or benzyl, n represents 1 or 2, and m represents zero, 1, or 2, and the resultant piperidines have the formula (II)

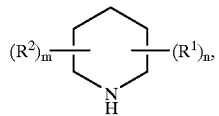

wherein $R^1$, $R^2$, m, and n are as defined under formula (I).

3. A process according to claim 2 wherein in formulas (I) and (II) $R^1$ represents COO—$C_1$–$C_4$-alkyl or two adjacent $R^1$ groups together represent a CO—N(benzyl)-CO group, $R^2$ represents $C_1$–$C_4$-alkyl, n represents 1 or 2, and m represents zero or 1.

4. A process according to claim 1 wherein the palladium-on-carbon catalyst comprises from 1 to 10% by weight of palladium.

5. A process according to claim 1 wherein an amount of catalyst is used such that from 0.5 to 30 mmol of palladium are present per mole of the pyridine.

6. A process according to claim 1 wherein the aromatic hydrocarbons are benzene, toluene, xylene, or other alkyl aromatics.

7. A process according to claim 1 wherein the temperatures are in the range from 20 to 200° C.

8. A process according to claim 1 wherein the pressures are in the range from 1 to 200 bar.

* * * * *